United States Patent [19]

Negus et al.

[11] Patent Number: 5,700,259
[45] Date of Patent: Dec. 23, 1997

[54] THORACOSCOPIC TRANSMYOCARDIAL REVASCULARIZATION HANDPIECE ASSEMBLY

[75] Inventors: Charles Christopher Negus; Stephen J. Linhares, both of Taunton, Mass.

[73] Assignee: PLC Medical Systems, Inc., Franklin, Mass.

[21] Appl. No.: 541,793

[22] Filed: Oct. 10, 1995

Related U.S. Application Data

[63] Continuation-in-part of Ser. No. 190,950, Feb. 3, 1994, which is a continuation-in-part of Ser. No. 201,052, Feb. 24, 1994, which is a continuation of Ser. No. 14,363, Feb. 5, 1993, abandoned, which is a continuation of Ser. No. 928,531, Aug. 13, 1992, abandoned, which is a continuation of Ser. No. 586,891, Sep. 24, 1990, abandoned.

[51] Int. Cl.$^6$ ..................................................... A61B 17/36
[52] U.S. Cl. ................... 606/14; 606/13; 606/17; 606/19
[58] Field of Search ........................... 606/7, 10–13, 606/17–19; 607/89

[56] References Cited

U.S. PATENT DOCUMENTS

| 1,135,465 | 4/1915 | Pollock . | |
|---|---|---|---|
| 3,865,113 | 2/1975 | Sharon et al. | 606/18 |
| 3,913,582 | 10/1975 | Sharon | 606/19 |
| 4,469,098 | 9/1984 | Davi | 606/7 |
| 4,917,083 | 4/1990 | Harrington et al. | 606/19 |
| 5,125,926 | 6/1992 | Rudko et al. | 606/19 |
| 5,200,604 | 4/1993 | Rudko et al. | 606/12 |

*Primary Examiner*—Michael Peffley
*Attorney, Agent, or Firm*—Iandiorio & Teska

[57] ABSTRACT

A thoracoscopic transmyocardial revascularization handpiece assembly for a medical laser system which includes a barrel which fits between the patient's ribs, a handpiece which fits between the ribs, a contacting surface on one end of the handpiece with a width which fits between the patient's ribs, and a contacting surface which has a length larger than the width resulting in a contact surface with a surface area which is greater than the cross-sectional area of the handpiece and which yet still fits between the patient's ribs.

19 Claims, 3 Drawing Sheets

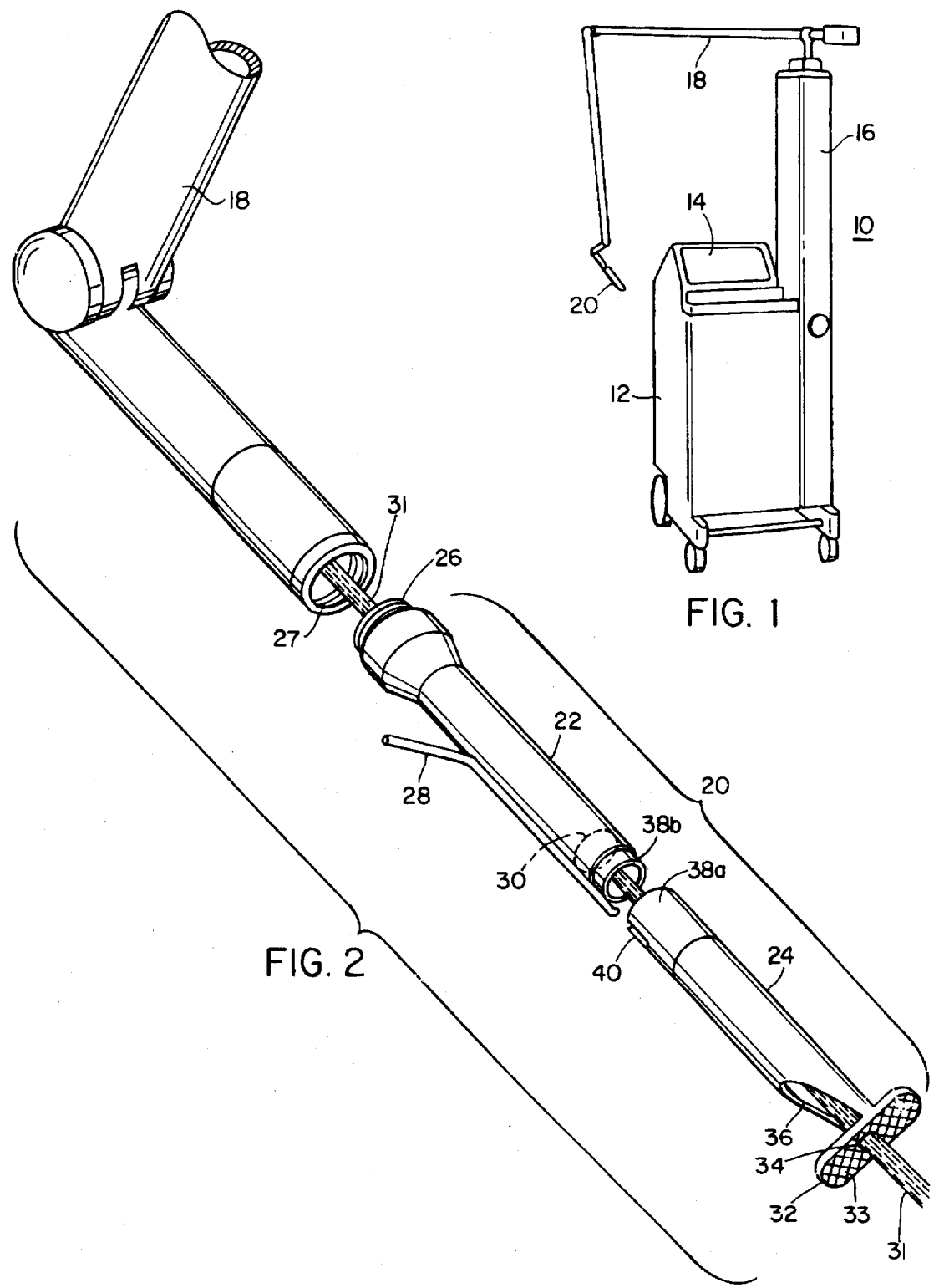

THORACOSCOPIC TRANSMYOCARDIAL REVASCULARIZATION HANDPIECE ASSEMBLY

RELATED CASES

This application is a continuation-in-part of Ser. No. 08/190,950 filed Feb. 3, 1994, which is a continuation-in-part of Ser. No. 08/201,052 filed Feb. 24, 1994, which is a continuation of Ser. No. 08/014,363 filed Feb. 5, 1993 (now abandoned), which is a continuation of Ser. No. 07/928,531 filed Aug. 13, 1992, (now abandoned) which is a continuation of Ser. No. 07/586,891 filed Sep. 24, 1990 (now abandoned). This application incorporates herein by reference the following patents having common inventors and assignee: application Ser. No. 586,885 filed Sep. 24, 1990, issued as U.S. Pat. No. 5,109,388, and application Ser. No. 586,951 filed Sep. 24, 1990, issued as U.S. Pat. No. 5,125,926.

FIELD OF INVENTION

This invention relates to a handpiece for a medical laser system such as a transmyocardial revascularization laser system, and more particularly to such a handpiece which is narrow enough to be slid between the ribs of the patient.

BACKGROUND OF INVENTION

Transmyocardial revascularization (TMR) is an alternative technique to bypass surgery for increasing blood flow to the heart muscle. TMR involves puncturing the heart wall with a laser to form a plurality of holes which heal on the outside but remain open on the inside of the heart to provide an alternative source of blood to the heart muscle. This technique has been used on a beating heart without the need to slow or still it. This has been accomplished with an innovative synchronizing approach disclosed in U.S. Pat. Nos. 5,125,926 and 5,109,388, incorporated herein by reference. The procedure is performed using a handpiece having a broad contacting wall and a knurled surface on the face of the contacting wall which allows the surgeon to properly align the handpiece on the heart wall and to avoid slipping of the handpiece during the procedures. However, as with any open heart surgical procedure, the rib cage of the patient must be opened up in order to provide access to the heart. This procedure is extremely invasive, can cause broken ribs, lengthy recovery periods and increased risk of infection, not only from the transmyocardial revascularization itself, but also from the opening of the chest cavity. While in some cases this type of invasive surgery may be unavoidable, in the case of an elderly patient, a less invasive procedure would cut down on the problems associated with this type of surgery.

SUMMARY OF INVENTION

It is therefore an object of this invention to provide an improved laser handpiece assembly for a laser system for transmyocardial revascularization.

It is a further object of this invention to provide such a laser handpiece assembly which eliminates the need to open the chest cavity to perform transmyocardial revascularization.

It is a further object of this invention to provide such a laser handpiece assembly which more readily maintains perpendicularity with the wall of a beating heart.

It is a further object of this invention to provide such a laser handpiece assembly which accurately locates the laser beam focal point at the correct point on the heart wall.

It is a further object of this invention to provide such a laser handpiece assembly which dissipates the laser plume to prevent interference with or damage to the laser beam lens.

It is a further object of this invention to provide such a laser handpiece assembly which prevents movement of the handpiece with respect to the heart wall.

The invention results from the realization that a truly effective thoracoscopic handpiece assembly for minimally invasive transmyocardial revascularization which reduces pain, bleeding, and the possibility of broken ribs or postoperative infection can be achieved with a narrow elongate handpiece which is slim enough to be slid between adjacent ribs for administering a laser beam to the heart wall and which is long enough to enable physician manipulation from outside the rib cage.

This invention features a thoracoscopic transmyocardial revascularization handpiece assembly for a medical laser system. There is an elongate barrel having a narrow width sized to fit between the ribs of a patient and having a first passage therethrough for conducting a surgical laser beam. There is an elongate handpiece extending from the barrel and having a similarly narrow width commensurate with the barrel and having a second passage therethrough connecting with the first passage for conducting a surgical laser beam. A contacting surface on the distal end of the handpiece contacts the wall of the patient's heart. The contacting surface has a width in a first dimension which is approximately that of the handpiece for fitting between the ribs of a patient and having a width in a second dimension which is larger to effect an area of the contacting surface which is substantially larger than the cross-sectional area of the handpiece. There is an aperture in the contacting surface communicating with the second passage for transmitting the laser beam, and there are focusing means in the barrel for focusing the laser beam proximate to the aperture to ablate the tissue of the heart wall and create a hole to the interior heart chamber.

In a preferred embodiment the barrel and the handpiece may be separate and there may be further included means for coupling the proximal end of the handpiece to the distal end of the barrel. The barrel and the handpiece may also be integral. The contacting surface may be knurled for preventing movement of the contacting wall with respect to the heart wall during surgery. The contacting surface may be at an angle to the longitudinal axis of the handpiece. For example, the contacting surface may be perpendicular to the longitudinal axis of the handpiece. The handpiece may further include a cutout portion proximate the contacting surface. The barrel may include means for introducing a purge gas into the handpiece to create a back pressure to force the ablated tissue out of the cutout portion and to keep the ablated tissue away from the focusing means. The contacting surface may be parallel to the longitudinal axis of the handpiece. The handpiece may further include deflecting means for directing the laser beam to the aperture. The handpiece may further include at least one port for exhausting the ablated tissue. The barrel may include means for introducing a purge gas into the handpiece to create backpressure to force the ablated tissue out of the at least one port and to keep the ablated tissue away from the focusing means. The means for coupling may include a friction fit between the proximal end of the handpiece and the distal end of the barrel. The barrel may further include means including an insulating portion for coupling the proximal end of the barrel to the laser system.

The invention also features a thoracoscopic transmyocardial revascularization handpiece assembly for a medical laser system which includes an elongate barrel having a narrow width to fit between the ribs of a patient and having a first passage therethrough for conducting a surgical laser beam. There is an elongate handpiece having a similarly narrow width commensurate with the barrel and having a second passage therethrough connecting with the first passage for conducting a surgical laser beam. There are means for coupling the proximal end of the handpiece to the distal end of the barrel. The contacting surface of the distal end of the handpiece contacts the wall of the patient's heart. The contacting surface has a width in the first dimension which is approximately that of the handpiece for fitting between the ribs of a patient, and having a width in a second dimension which is larger to effect an area of the contacting surface which is substantially larger than the cross-sectional area of the handpiece. There is an aperture in the contacting surface communicating with the second passage for transmitting the laser beam and there are focusing means in the barrel for focusing the laser beam proximate to the aperture to ablate the tissue of the heart wall and create a hole in the interior of the heart chamber.

DISCLOSURE OF PREFERRED EMBODIMENT

Other objects, features and advantages will occur to those skilled in the art from the following description of a preferred embodiment and the accompanying drawings, in which:

FIG. 1 is a three-dimensional view of a laser system which utilizes the handpiece assembly of this invention;

FIG. 2 is an enlarged, more detailed, exploded three-dimensional view of a portion of the articulated arm in FIG. 1 and a first embodiment of the invention;

Figure 3:
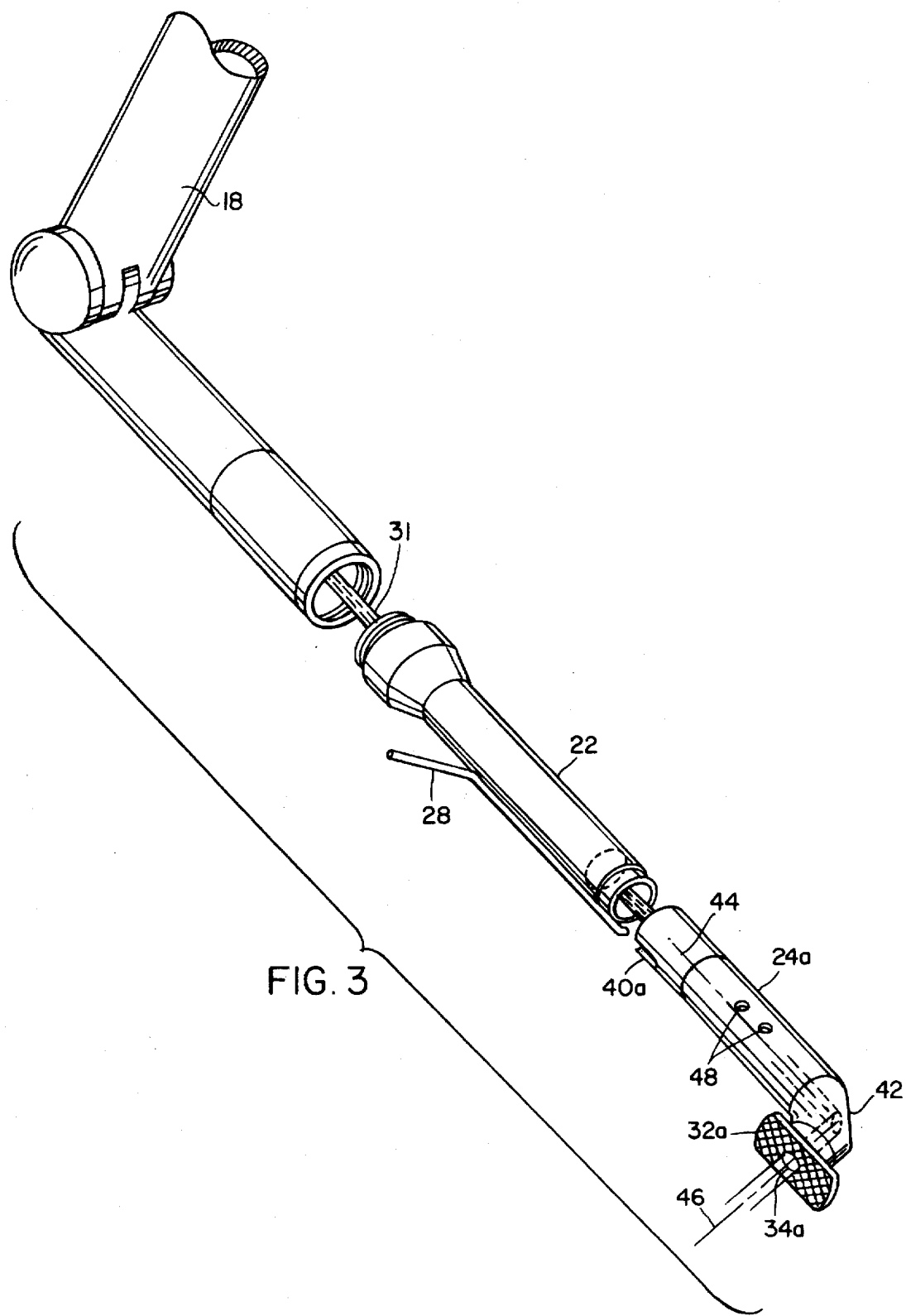
FIG. 3 is an enlarged, more detailed, exploded three-dimensional view of a portion of the articulated arm in FIG. 1 and a second embodiment of the invention.

There is shown in FIG. 1 a surgical laser system 10 which includes a power supply and control 12 operated through control and monitor screen 14 to operate laser 16. The output from laser 16 is directed through articulated arm 18 to handpiece assembly 20 typically held by the operator or surgeon to direct the beam at the desired target.

Handpiece assembly 20, FIG. 2, includes barrel 22 and handpiece 24. Barrel 22 includes threaded portion 26 for connection to articulated arm 18 at threaded portion 27, and purge tube 28 for introducing a purge gas into handpiece 24. Handpiece 24 includes contacting wall 32 having a knurled surface 33 for preventing slippage of handpiece 24 on the heart during surgery. There is an aperture 34 substantially centered in contacting wall 32 through which laser beam 31 exits to strike the heart. Lens 30, shown in phantom in barrel 22, focuses laser beam 31 at a predetermined distance, typically at or near aperture 34. Handpiece 24 also includes cutout portion 36 through which the user can view the beam as it enters aperture 34. Cutout portion 36 also acts as a venting hole for the ablative plume which rises from the heart or other tissue struck by the laser beam 31. Handpiece 24 includes coupling portion 38a which slides over coupling portion 38b of barrel 22 in order to effect a friction fit. There is a slot 40 in coupling portion 38a which accepts the distal end of purge tube 28.

In accordance with this invention, barrel 22 and handpiece 24 typically have diameters in the range of ⅜ inch to ⅝ inch. This allows the handpiece assembly to be slid between adjacent ribs of a patient in order to access the heart without opening the chest cavity. Generally, the space between ribs of a patient is approximately 0.5". As can be seen in the figure, contacting wall 32 of handpiece 24 is formed such that the width of the contacting wall is the same as the diameter of handpiece 24 while the length of contacting wall 32 is approximately twice the diameter of handpiece 24. This increases the area of contact with the heart and therefore decreases the pressure of force per unit area on the heart. It also provides a more stable platform by which to maintain perpendicularity between the beam 31 and the heart wall and reduces the chances of the handpiece puncturing or otherwise damaging the heart tissue. However, the narrow width of contacting wall 32 allows handpiece assembly 20 to be slid between adjacent ribs of the patient.

Purge tube 28 is connected to a purge gas source which provides a gas such as carbon dioxide under a gentle flow, typically one to three liters per minute, to create a back pressure from lens 30 forward into handpiece 24. This keeps any debris from the ablation from contacting and obscuring or damaging lens 30.

Although handpiece assembly 20 has been shown with handpiece 24 as a straight member, this is not a necessary limitation of the invention: handpiece 24 may be constructed at any desired angle, For example, handpiece 24a, FIG. 3, may include a right angle configuration so that contacting wall 32a and aperture 34a are facing at a right angle to the path of laser beam 31. A reflective surface 42 is provided to reflect the beam from an incoming path parallel to axis 44 to the outgoing path parallel to axis 46. One or more vent holes 48 may be provided for exhausting gas and ablated tissue aided by the back pressure caused by the introduction of the purge gas through purge tube 28. In this embodiment, reflective surface 42 is enclosed as much as possible in order to minimize contamination from body fluids prior to firing the laser.

In the preferred embodiment, barrel 22 is formed of stainless steel due to its strength, its ability to be sterilized repeatedly and its ability to withstand heat from the unfocused laser before it is focus by lens 30. Purge tube 28 is also formed of stainless steel and is typically welded to barrel 22. Handpiece 24 is typically injection molded of medical grade clear acrylic. This allows the surgeon to monitor the laser beam as it passes through the handpiece, allows more effective cleaning of the inside of the handpiece during surgery and enhances the disposability of the handpiece. Coupling portion 38a of handpiece 24, however, is formed of the same stainless steel as barrel 22. This allows for a tighter friction fit between handpiece 24 and barrel 22 which is not affected by changes in temperature due to the heat of the laser. Threaded portion 26 of barrel 22 is typically formed of an electrical insulating material such as Delrin to electrically insulate the patient from the laser system, and to avoid additional grounding locations for electrocautery devices used on the patient. Also, lens 30 has a five-inch focal length which focuses beam 31 at aperture 34 in the case of the embodiment of FIG. 2 and at aperture 34a in the case of the embodiment of FIG. 3.

Figure 4:
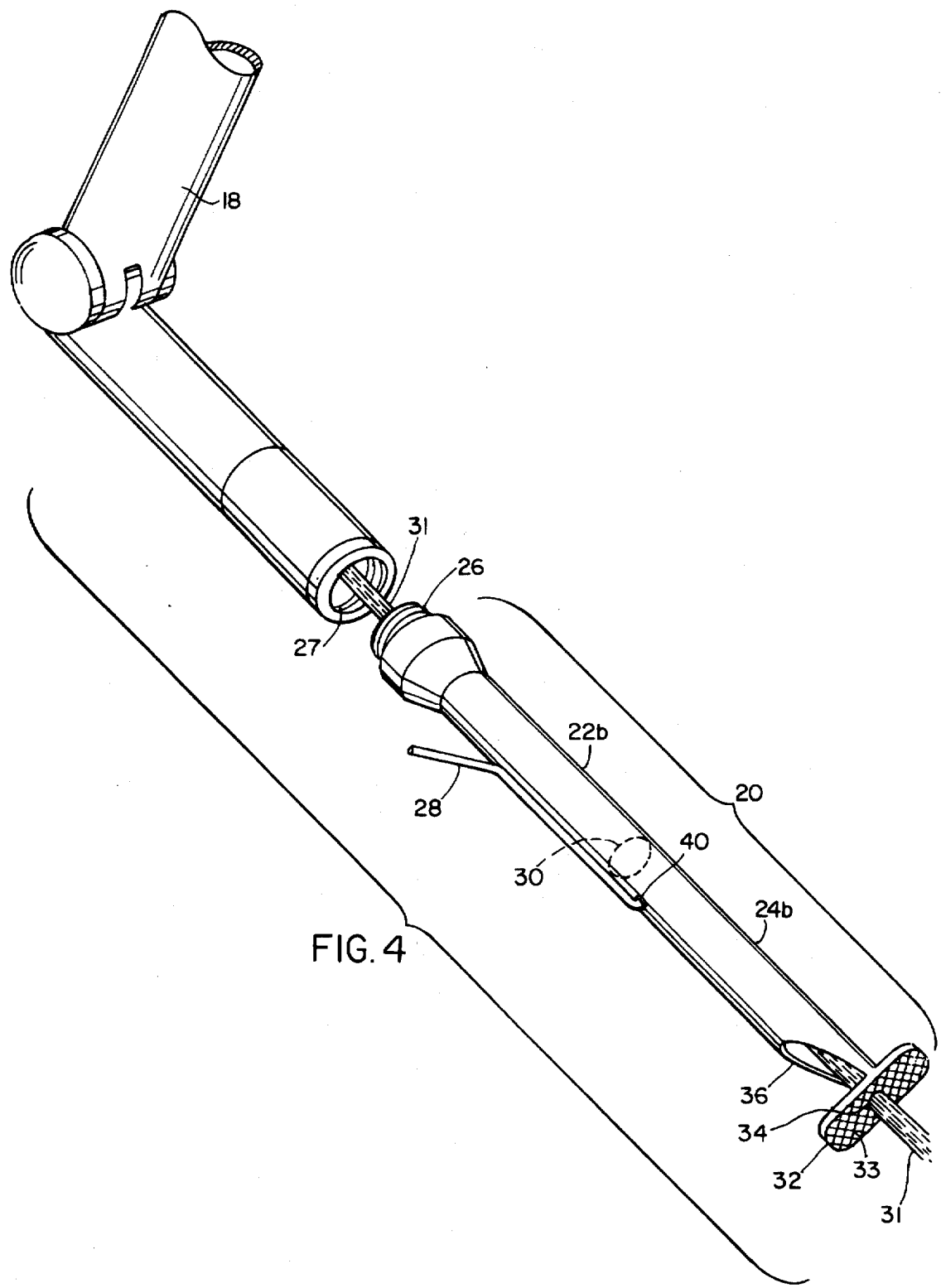
FIG. 4 is an enlarged, more detailed exploded three-dimensional view of a portion of the articulated arm in FIG. 1 and another embodiment of the invention in which the band and handpiece are integral.

While handpiece assembly 20, FIGS. 2 and 3, has been shown as including two separate sections, barrel 22 and handpiece 24 (24a), that is not a necessary limitation of the invention. Handpiece assembly 20b, FIG. 4, may be made as a single integral unit including both barrel 22b and handpiece 24b.

Although specific features of this invention are shown in some drawings and not others, this is for convenience only as each feature may be combined with any or all of the other features in accordance with the invention.

Other embodiments will occur to those skilled in the art and are within the following claims:

What is claimed is:

1. A thoracoscopic transmyocardial revascularization handpiece assembly for a medical laser system, comprising:
   an elongate barrel having a narrow width sized to fit between the ribs of a patient and having a first passage therethrough for conducting a surgical laser beam;
   an elongate handpiece extending from said barrel and having a similarly narrow width commensurate with said barrel and having a second passage therethrough connecting with said first passage for conducting a surgical laser beam;
   a contacting surface on a distal end of said handpiece for contacting the wall of the patient's heart; said contacting surface having a width in a first dimension which is approximately that of said handpiece for fitting between the ribs of a patient and having a width in a second dimension which is larger to effect an area of said contacting surface which is substantially larger than the cross-sectional area of said handpiece to provide a more stable platform to maintain perpendicularity between the laser beam and the wall of the heart;
   an aperture substantially centered in said contacting surface communicating with said second passage for transmitting the laser beam; and
   focusing means in said barrel for focusing the laser beam proximate to the aperture to ablate the tissue of the heart wall and create a hole to the interior heart chamber.

2. The thoracoscopic transmyocardial revascularization handpiece assembly of claim 1 in which said barrel and said handpiece are separate and there is further included means for coupling a proximal end of said handpiece to the distal end of said barrel.

3. The thoracoscopic transmyocardial revascularization handpiece assembly of claim 1 in which said barrel and said handpiece are integral.

4. The thoracoscopic transmyocardial revascularization handpiece assembly of claim 1 in which said contacting surface is knurled for preventing movement of said contacting surface with respect to the heart wall during surgery.

5. The thoracoscopic transmyocardial revascularization handpiece assembly of claim 1 in which said contacting surface is at an angle to the longitudinal axis of said handpiece.

6. The thoracoscopic transmyocardial revascularization handpiece assembly of claim 4 in which said contacting surface is perpendicular to the longitudinal axis of said handpiece.

7. The thoracoscopic transmyocardial revascularization handpiece assembly of claim 6 in which said handpiece further includes a cutout portion proximate said contacting surface.

8. The thoracoscopic transmyocardial revascularization handpiece assembly of claim 7 in which said barrel includes means for introducing a purge gas into said handpiece to create a back pressure to force said ablated tissue out of said cutout portion and to keep said ablated tissue away from said focusing means.

9. The thoracoscopic transmyocardial revascularization handpiece assembly of claim 4 in which said contacting surface is parallel to the longitudinal axis of said handpiece.

10. The thoracoscopic transmyocardial revascularization handpiece assembly of claim 9 in which said handpiece further includes deflecting means for directing said laser beam to said aperture.

11. The thoracoscopic transmyocardial revascularization handpiece assembly of claim 10 in which said handpiece further includes at least one port for exhausting said ablated tissue.

12. The thoracoscopic transmyocardial revascularization handpiece assembly of claim 11 in which said barrel includes means for introducing a purge gas into said handpiece to create a back pressure to force said ablated tissue out of said at least one port and to keep said ablated tissue away from said focusing means.

13. The thoracoscopic transmyocardial revascularization handpiece assembly of claim 2 in which said means for coupling includes a friction fit between a proximal end of said handpiece and said distal end of said barrel.

14. The thoracoscopic transmyocardial with said second passage for transmitting the laser beam; and
   focusing means in said barrel for focusing the laser beam proximate to the aperture to ablate the tissue of the heart wall and create a hole to the interior heart chamber.

15. A thoracoscopic transmyocardial revascularization handpiece assembly for a medical laser system, comprising:
   an elongate barrel having a narrow width sized to fit between the ribs of a patient and having a first passage therethrough for conducting a surgical laser beam;
   an elongate handpiece having a similarly narrow width commensurate with said barrel and having a second passage therethrough connecting with said first passage for conducting a surgical laser beam;
   means for coupling the proximal end of said handpiece to the distal end of said barrel;
   a contacting surface on the distal end of said handpiece for contacting the wall of the patient's heart; said contacting surface having a width in a first dimension which is approximately that of said handpiece for fitting between the ribs of a patient and having a width in a second dimension which is larger to effect an area of said contacting surface which is substantially larger than a cross-sectional area of said handpiece to provide a more stable platform to maintain perpendicularity between the laser and the wall of the heart;
   an aperture substantially centered in said contacting surface communicating with said second passage for transmitting the laser beam; and
   focusing means in said barrel for focusing the laser beam proximate to the aperture to ablate the tissue of the heart wall and create a hole to the interior heart chamber.

16. A thoracoscopic transmyocardial revascularization handpiece assembly for a medical laser system, comprising:
   an elongate barrel having a narrow width sized to fit between the ribs of a patient and having a first passage therethrough for conducting a surgical laser beam;
   an elongate handpiece extending from said barrel and having a similarly narrow width commensurate with said barrel and having a second passage therethrough connecting with said first passage for conducting a surgical laser beam;
   a knurled contacting surface on a distal end of said handpiece for contacting the wall of the patient's heart, said contacting surface being parallel to the longitudinal axis of said handpiece and having a width in a first dimension which is approximately that of said handpiece for fitting between the ribs of a patient and having a width in a second dimension which is larger to effect an area of said contacting surface which is substantially larger than a cross-sectional area of said handpiece to provide a more stable platform to maintain perpendicularity between the laser and the wall of the heart;

an aperture substantially centered in said contacting surface communicating with said second passage for transmitting the laser beam; and focusing means in said barrel for focusing the laser beam proximate to the aperture to ablate the tissue of the heart wall and create a hole to the interior heart chamber.

17. The thoracoscopic transmyocardial revascularization handpiece assembly of claim 16 in which said handpiece further includes deflecting means for directing said laser beam to said aperture.

18. The thoracoscopic transmyocardial revascularization handpiece assembly of claim 17 in which said handpiece further includes at least one port for exhausting said ablated tissue.

19. The thoracoscopic transmyocardial revascularization handpiece assembly of claim 18 in which said barrel includes means for introducing a purge gas into said handpiece to create a back pressure to force said ablated tissue out of said at least one port and to keep said ablated tissue away from said focusing means.

* * * * *